United States Patent [19]

Call

[11] Patent Number: 5,403,723
[45] Date of Patent: Apr. 4, 1995

[54] PROCESS FOR THE PRODUCTION OF LIGNOLYTIC ENZYMES BY MEANS OF WHITE ROT FUNGI

[76] Inventor: Hans-Peter Call, Heinsberger Strasse 14a, D-5132 Übach-Palenberg, Germany

[21] Appl. No.: 211,758
[22] PCT Filed: Oct. 19, 1992
[86] PCT No.: PCT/EP92/02398
§ 371 Date: Jun. 10, 1994
§ 102(e) Date: Jun. 10, 1994
[87] PCT Pub. No.: WO93/08272
PCT Pub. Date: Apr. 29, 1993

[30] Foreign Application Priority Data
Oct. 21, 1991 [DE] Germany .............. 41 34 716.1

[51] Int. Cl.$^6$ .................... C12N 9/08; C12P 39/00
[52] U.S. Cl. .................... 435/42; 435/71.1; 435/171; 435/174; 435/192; 435/911
[58] Field of Search .............. 435/42, 192, 174, 911, 435/171, 71.1

[56] References Cited

U.S. PATENT DOCUMENTS

| | | | |
|---|---|---|---|
| 5,153,121 | 10/1992 | Asther et al. | 435/71.1 |
| 5,200,338 | 4/1993 | Crawford et al. | 435/192 |
| 5,203,964 | 4/1993 | Call | 435/278 |
| 5,278,058 | 1/1994 | Call | 435/192 |
| 5,342,765 | 8/1994 | Irvine et al. | 435/71.1 |

FOREIGN PATENT DOCUMENTS 2600077 12/1987 France .
9004021 4/1990 WIPO .

OTHER PUBLICATIONS

Journal of Biotechnology, Bd. 8, No. 2, Jun. 1988, Amsterdam, The Netherlands, pp. 163–170.
Chemical Abstracts, vol. 109, No. 13, Sep. 26, 1988, Columbus, Ohio, Abstract No. 108861.
Journal of Biotechnology, Bd. 8, No. 2, Jun. 1988, Amsterdam, The Netherlands, pp. 97–112.

Primary Examiner—Herbert J. Lilling
Attorney, Agent, or Firm—Friedrich Kueffner

[57] ABSTRACT

The present invention relates to a process for the production of lignolytic enzymes by means of white rot fungi. In the process, a culture composed of the fungi of the subclass of the Aphyllophorales is placed in a closed fermentation vessel filled with a nutrient solution and the suspension is gently moved for the production of pellets of Aphyllophorales, such that there cannot be any shearing forces which would destroy the pellets, wherein the enzymes are produced with the addition of yeasts or benzaldehydes, chlorobenzaldehydes, nitrobenzaldehydes, hydroxybenzaldehydes, aminobenzaldehydes, methylbenzaldehydes, diaryls or triaryls, dialkylalkanes, trialkyl alkanes, open-chained or cyclic imines or derivatives of the aforementioned substances as inductive compounds, wherein the induction may take place one time or several times, and the enzymes are subsequently harvested.

5 Claims, 2 Drawing Sheets

PROCESS FOR THE PRODUCTION OF LIGNOLYTIC ENZYMES BY MEANS OF WHITE ROT FUNGI

The present invention relates to a process for the production of lignolytic enzymes by means of white rot fungi from the subclass of the Aphyllophorales.

During the last ten years, it has frequently been attempted to use white rot fungi for the production of lignolytic enzymes on an industrial scale. In this regard, Phanerochaete chrysosporium were at the center of attention.

For example, there are experiments carried out in the stirring fermenter (H. Janshekar und A. Fiechter, Journal of Biotechnology 8 (1988), 9714 112). However, these experiments were not successful because the pellets formed by Phanerochaete chrysosporium in the stirring fermenter were shattered time and again. However, since Phanerochaete chrysosporium produces enzymes only when it is present in the form of pellets or in the immobilized state, optimum enzyme production cannot be achieved by the conventional processes in the stirring fermenter.

Moreover, biotechnology has developed reactors intended especially for sensitive cells. Thus, a so-called vibromixer has been developed which is suitable even for sensitive animal cells and plant cells (Einsele, Finn, Samhaber: Mikrobiologische und biochemische Verfahrenstechnik (Microbiological and Biochemical Technology), Weinheim 1985, p. 150; Einsele: Chem. Ing. Tech. 45 (1973), 1368; Rehm: Chem. Ing. Tech. 42 (1970), 583). The action of the vibromixer is based on the Bernoulli effect. Instead of the stirrer, a horizontally extending plate attached to a vertical shaft is arranged in the interior of the vessel. The plate has four holes which narrow downwardly. The plate is moved up and down by means of the shaft. This causes pressure differences in the four holes because the liquid flows back in the openings from the large diameter to the small diameter. While the cells are moved well in that manner, there is essentially no damage. However, a vibromixer of this type has the disadvantage that it still does not operate gently enough for the sensitive pellets of Phanerochaete chrysosporium. In addition, up to today, vibromixers of this type cannot be used on a large commercial scale.

Finally, glass vessels moved by mechanical shakers are also suitable for the formation of pellets of microorganisms (H. J. Rehm: Einführung in die industrielle Mikrobiologie (Introduction into Industrial Microbiology), Berlin-Heidelberg-New York 1971). For this purpose, the vessels (usually bottles or Erlenmeyer flasks) are clamped in the machines in several tiers above each other. The shaking movement of the vessels causes air to be whipped into the solution from the surface. Amplitude machines, rotation machines and vibration machines which usually have variable speeds are used for shaking. The vessels may be provided with planar bulges, the so-called baffle plates. These systems have the disadvantage that they are only suitable for the laboratory scale. For a large-scale commercial application, thousands of bottles or Erlenmeyer flasks would be necessary, so that the use of such devices is economically not feasible.

In order to solve the above-mentioned problems of the use of stirring reactors, it has been increasingly attempted to operate with immobilized cells (S. Linko, Journal of Biotechnology, 8 (1988), 163–170; H. Willerhausen, A. Jäger, H. Graf, Journal of Biotechnology, 6 (1987), 239–243; Y. Linko, M. Leisola, N. Lindholm, J. Troller, P. Linko. A. Fiechter, Journal of Biotechnology, 4 (1986), 283–291). However, these attempts also failed when larger volumes were involved. As a rule, these processes could no longer be carried out when the fermenter volume was more than 40 l. The reason for this can essentially be found in the fact that Phanerochaete chrysosporium in pellet form has an optimum surface and, thus, produces enzymes best when it is present in this state.

A novel reactor has been specifically developed for solving the above-mentioned problems in the use of Phanerochaete chrysosporium for the production of lignolytic enzymes. This reactor is the subject matter of the prior, but not prepublished, German patent application P 40 12 743. The reactor includes a closed fermentation vessel without stirrer which is suspended freely rotatably and slewably in a cardanic mounting arrangement. A drive motor is arranged underneath the vessel, wherein the drive shaft of the drive motor is connected to the bottom of the vessel by means of an eccentric. The eccentric makes it possible to adjust the angle of inclination and the oscillation amplitude of the vessel. Thus, rotating and slewing movements of the vessels can be achieved by means of the infinitely variably adjustable motor.

In the fermenter moved in this manner, Phanerochaete chrysosporium forms pellets which are not continuously destroyed by mechanical influences. As a result, the pellets obtain an optimum shape for the enzyme production. Since, on the other hand, the cardanic mounting of the reactor with minimum oscillations makes it possible to construct reactors having volumina of between 1 and 3 cubic meters, a production of lignolytic enzymes can be carried out in the above-described arrangement on a commercial scale with yields which have in the past been considered impossible.

However, the results of the production by means of this fermenter are still not satisfactory. This is because the yields still not have reached volumina which would make a large-scale commercial production profitable.

Therefore, it is the object of the present invention to provide an improved process for the production of lignolytic enzymes by means of white rot fungi, wherein a culture composed of the fungi of the subclass of the Aphyllophorales is placed in a closed fermentation vessel filled with a nutrient solution and the suspension is gently moved for the production of pellets of Aphyllophorales, such that there cannot be any shearing forces which would destroy the pellets, and wherein the process can be carried out even in fermentation vessels having a volume of more than 40 l and ensures significantly raised enzyme yields as compared to the previous state of the art.

This object is met by producing the enzymes with the addition of yeasts or benzaldehydes, chlorobenzaldehydes, nitrobenzaldehydes, hydroxybenzaldehydes, aminobenzaldehydes, methylbenzaldehydes, diaryls or triaryls, dialkylalkanes, trialkyl alkanes, open-chained or cyclic imines or derivatives of the aforementioned substances as inductive compounds, wherein the induction may take place one time or several times. Subsequently, the enzymes are harvested.

As compared to the previous state of the art, the use of a mixed culture composed of Aphyllophorales and yeasts results in a significant increase of the enzyme production. The yeasts added to the culture are subjected to almost complete lysis during the process by the Aphyllophorales. The substantial amounts of released yeast components, for example, cell wall components and yeast glucanes, probably have protective colloid character and can, as a result, cause an increase of the enzyme production.

It is known from the prior art that various chemical substances can act as inductors in fermentation solutions. Thus, the laccase yields can be improved by xylidine. However, these substances and similar substances can hardly be used on a large commercial scale because of their high toxicity, so that this possibility of enzyme increase has not been used in the past. Now, in accordance with the invention, a new group of inductors have been found which do not have these disadvantages. They are benzaldehydes, chlorobenzaldehydes, nitrobenzaldehydes, hydroxybenzaldehydes, aminobenzaldehydes, methylbenzaldehydes, diaryls, triaryls, dialkylalkanes, trialkylalkanes, open-chained or cyclic imines. The derivatives of the aforementioned compounds can also be used. These materials surprisingly do not have the aforementioned disadvantages. But they are particularly also suitable for use on a large commercial scale. It is particularly surprising that very high enzyme yields can be achieved (about 2,000 IU/ml enzyme) by the use of the aforementioned inductors.

The above-described surprisingly improved enzyme yields can already be observed when using the mixtures of Aphyllophorales with yeasts or the above-listed inductors in conventional stirring fermenters. However, these stirring fermenters must be equipped with a special stirrer whose paddles can be adjusted, so that hardly any shearing forces occur during stirring which could destroy the formed pellets. Accordingly, important for the invention are the shape of the stirrer, on the one hand, and the possibility of adjusting the paddles, on the other hand.

However, the enzyme yields are particularly good if the above-described reactor according to German patent application P 40 12 743 is used. This is because the already significantly increased enzyme yields when using this fermenter can be even further increased in a surprising manner by using a mixture of Aphyllophorales and yeasts or the specially inductively acting compounds, wherein the induction can be carried out one time or several times.

In accordance with a variation of the process, the pellets are initially produced in the shaking fermenter with the addition of yeast or benzaldehydes and subsequently the suspension containing the pellets is transferred to a stirring fermenter. In the stirring fermenter, the enzymes are then produced by means of the pellets. It is also to be considered advantageous that, after the conclusion of the enzyme production in the shaking fermenter or in the stirring fermenter, the separated pellets of the Aphyllophorales can directly be used again for the enzyme production. For this purpose, it is useful to separate the pellets from the remaining suspension and to return the pellets to the fermenter after the separation of the enzyme. In accordance with the invention, the separation can be carried out by means of ultrafiltration. In a preferred embodiment according to the invention, Phanerochaete chrysosporium is used in a mixture with yeasts. In this case, when used in the stirring fermenter, peak values of about 1,000 IU/l culture can be achieved. When used in the shaking fermenter, these values are 1,500–2,000 IU/l (1 IU=turnover per 1 micromol veratryl alcohol/min./ml enzyme in veratryl aldehyde).

Before carrying out the process according to the invention, Phanerochaete chrysosporium can be advantageously cultivated in Petri dishes and then in standing cultures. The mycelia formed in this manner are subsequently crushed and used in the process according to the invention. The cultivation of Phanerochaete chrysosporium is carried out under the known conditions. Thus, the cultivation is usually carried out at temperatures of 37°–40° C. and a pH value of 4.5 to 5. The preferred pH value is 5. The preferred cultivating temperature is 37° C.

The following composition has been found useful as a substrate for the culture of Phanerochaete chrysosporium in a mixture with yeasts:

Pre-culture medium

1) Mineral salt solution (ME): (per liter) 10.5 g nitrilo triacetate; 21 g $MgSO_4$, 3.5 g $MnSO_4$; 7 g NaCl, 0.7 g $FeSO_4$; 0.7 g $CoCl_2$; 0.7 g $CaCl_2$; 0.7 g $ZnSO_4$; 0.07 g $CuSO_4$, 0.07 g $AlK_2SO_4$; 0.07 g $H_3BO_3$; 0.07 g $NaMoO_4$.

2) Solution 1 (salt solution) (per liter) 20 g $KH_2PO_4$; 5 g $MgSO_4$; 1 g $CaCl_2$.

3) Buffer (pH 4.5–5.5) 1 m $NaH_2PO_4/Na_2HPO_4$-buffer composition per 1 l of medium:
  0.2 g ammonium tartrate
  100 ml solution 1
  1.43 ml ME solution
  10 g glucose
  10 ml buffer
  +0.9 ml thiamine 100 mg/l (is added in sterilely filtered form after treatment in the autoclave)

Main culture medium

Composition per 1 medium:
  0.2 g ammonium tartrate
  100 ml solution 1
  10 ml ME solution
  10 g glucose
  10 ml buffer
  67.3 mg veratryl alcohol
  2 ml Tween 80
  +0.9 ml thiamine (100 mg/l)

In accordance with another preferred embodiment of the invention, Coriolus versicolor is used in combination with the above-listed inductors, particularly benzaldehydes, or their derivatives. It is known from the state of the art that good laccase yields can be achieved with inductors, for example, xylidine. However, for the reasons mentioned above, these inductors have not proved useful. By using the inductors according to the invention in combination with Coriolus versicolor, it is now possible in a surprising manner to achieve increases of the enzyme yield of up to 100%. The invention is described in the following in more detail with reference to figures:

Figure 1:
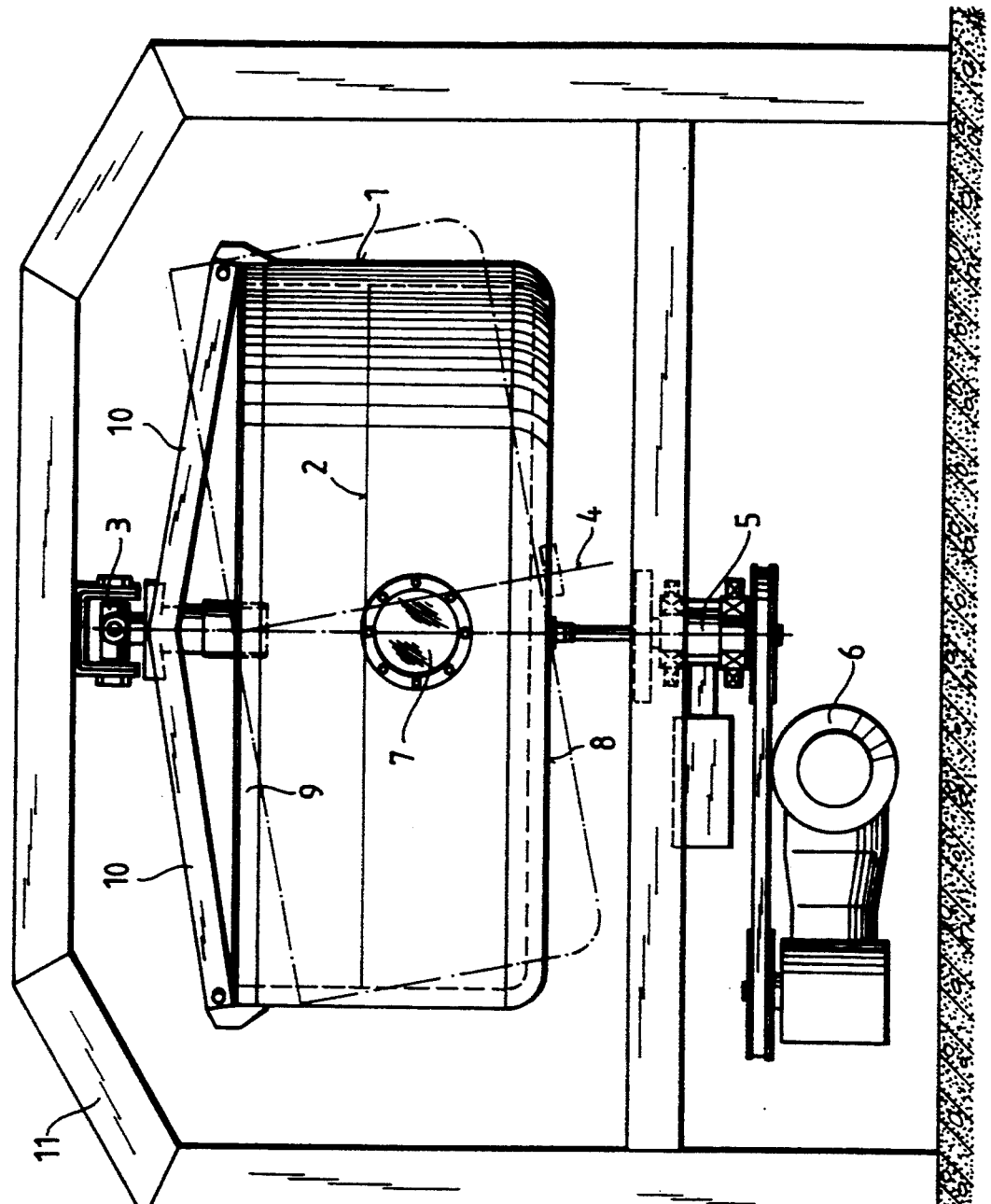
FIG. 1 shows the fermenter without stirrer used in accordance with the invention.

The reactor without stirrer illustrated in FIG. 1 is employed primarily for the production of the pellets of Aphyllophorales and possibly for the production of the enzymes. The formation of the pellets takes place in the vessel 1. The vessel 1 is a closed container with a solid bottom 8, side walls, cover 9 and a viewing window 7. Openings for various measuring sensors ($O_2$, pH, antifroth) and for feeding and withdrawing of substrate and vaccination cultures are provided on the sides or in the bottom. The vessel 1 is suspended in a frame 11. The vessel 1 is fastened by means of the gripping arms 10. The vessel 1 is suspended freely rotatably and slewably in the cardanic mounting arrangement by means of the gripping arms 10. The rotating and slewing movements are effected by the motor 6. The motor 6 is connected to the bottom 8 of the vessel 1 by means of the drive shaft 5 and the eccentric 4. The angle of inclination and the oscillation amplitude of the vessel 1 are adjusted by means of the eccentric 4. The speed of the rotating and slewing movements of the vessel 1 can be adjusted by the rate of rotation of the motor.

Figure 2A:
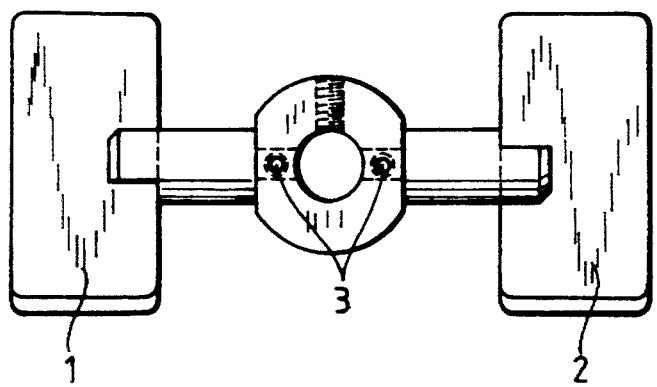
FIG. 2a shows in a view from above the special configuration of a stirrer for use in the process according to the invention.
Figure 2B:
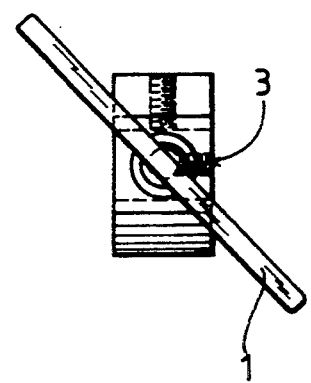
FIG. 2b shows the stirrer in a transverse view.
Figure 2C:
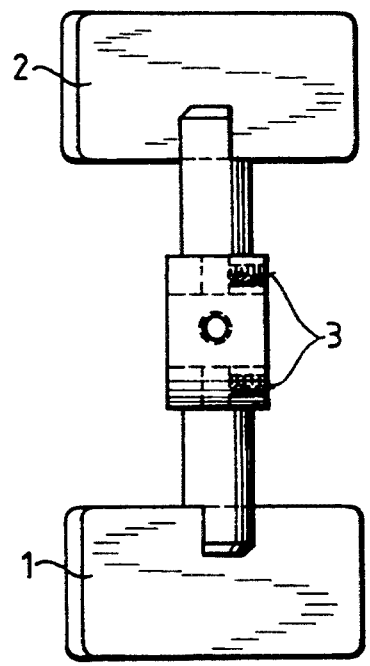
FIG. 2c shows the stirrer in a view from the side.

The stirrer illustrated in FIGS. 2a–2c is equipped with the two paddles 1 and 2. The angle of inclination of the paddles can be changed by means of the adjusting screw 3. In this manner, the stirrer can always be adjusted exactly in accordance with the sensitivity of the cells employed, so that no shearing forces can occur which could destroy the pellets.

The invention is explained in more detail with the aid of the following examples:

EXAMPLE 1

Phanerochaete chrysosporium ATCC 32629 is used as strain. First, malt agar slabs are vaccinated and then cultivated at 27° C. for approx. 10–12 days. Half of the growth is removed from these slabs, and a 50 ml standing culture is vaccinated in a 500 ml Erlenmeyer flask (cultivation time approx. 5 days at 37° C.). The pre-culture thus obtained is decanted, filled up again to the original volume with a.dest. and then shredded in a Braun Starmix at stage 3 for 2×30 seconds. 15 ml of pre-culture are added per liter of medium in the shaking reactor, i.e. 75 ml are added to a 10 l shaking reactor being filled with 5 l. Yeasts are added in an amount of $0.5-0.8 \times 2-4 \times 10^5$/ml medium. The cultivation temperature is 38° C., the shaking frequency is 90 rpm and the deflection is approx. 5 cm. Each day, it is gassed with $O_2$ for 30 seconds (100 l/hour). The cultivation period is 4–5 days. The enzyme yields are approx. 1500–2000 IU/l (1 IU=1 μmole turnover of veratryl alcohol to veratryl aldehyde/min.).

The media are composed as follows:

Pre-culture medium

1) Mineral salt solution (ME): (per liter) 10.5 g nitrilo triacetate; 21 g $MgSO_4$, 3.5 g $MnSO_4$; 7 g NaCl, 0.7 g $FeSO_4$; 0.7 g $CoCl_2$; 0.7 g $CaCl_2$; 0.7 g $ZnSO_4$; 0.07 g $CuSO_4$, 0.07 g $AlK_2SO_4$; 0.07 g $H_3BO_3$; 0.07 g $NaMoO_4$.

2) Solution 1 (salt solution) (per liter) 20 g $KH_2PO_4$; 5 g $MgSO_4$; 1 g $CaCl_2$.

3) Buffer (pH 4.5–5.5) 1 m $NaH_2PO_4/Na_2HPO_4$-buffer composition per 1 l of medium:
  0.2 g ammonium tartrate
  100 ml solution 1
  1.43 ml ME solution
  10 g glucose
  10 ml buffer
  +0.9 ml thiamine 100 ml/l (is added in sterilely filtered form after treatment in the autoclave)

Main culture medium

Composition per 1 medium:
  0.2 g ammonium tartrate
  100 ml solution 1
  10 ml ME solution
  10 g glucose
  10 ml buffer
  67.3 mg veratryl alcohol
  2 ml Tween 80
  +0.9 ml thiamine (100 mg/l)

EXAMPLE 2

Phanerochaete chrysosporium ATCC 32629 is used as strain. First, malt agar slabs are vaccinated and then cultivated at 27° C. for approx. 10–12 days. Half of the growth is removed from these slabs, and a 50 ml standing culture is vaccinated in a 500 ml Erlenmeyer flask (cultivation time approx. 5 days at 37° C.). The pre-culture thus obtained is decanted, filled up again to the original volume with a.dest. and then shredded in a Braun Starmix at stage 3 for 2×30 seconds. 15 ml of pre-culture are added per liter of medium in the stirring reactor, i.e. 75 ml are added to a 10 l shaking reactor being filled with 5 l. Yeasts are added in an amount of $2-4 \times 10^5$/ml medium. The cultivation temperature is 38° C., the stirring frequency is 110 rpm.

The partial oxygen pressure of the culture is maintained at 30–70% by means of $O_2$-measurement using $O_2$-electrode and controls. The cultivation period is 4 to 5 days. The enzyme yields are up to 1,000 IU/l.

EXAMPLE 3

Coriolus versicolor ATCC 34671 is used as strain. A mycelium agar piece having a size of approx. 1 cm in diameter is taken from an inclined malt agar tube by means of a cork borer and placed on the center of a malt agar slab and is cultivated for approx. 8 days (28° C.). Three pieces having a diameter of 1 cm each are punched from this slab and are placed with the mycelium side facing upwardly on a 50 ml standing culture (in a 300 ml Erlenmeyer flask). Cultivation is for approx. 8 days at 28° C. The mycelium growth produced in this manner is separated from the standing culture liquid and is mixed in a Braun Starmix (stage 3) for 2×30 seconds.

30–60 ml pre-culture medium are used as an inoculate per 1 medium. After 3–4 days cultivation time, 10–20 ml of a 1% solution of 2-aminobenzaldehyde in 50% alcohol are used as inductor. The entire cultivation period is 6 days.

The composition reproduced below can be used as medium:

A. Solutions
Solution 1:
  10 g $KH_2PO_4$
  5 g $MgSO_4 \times 7\ H_2O$
  1 g $Na_2HPO_4 \times 2\ H_2O$
  dissolved in 1000 ml a.dest.
Mineral-Solution:
  1 g $CaCl_2$
  1 g $FeSO_4 \times 7\ H_2O$
  0.2 g $CuSO_4 \times 5\ H_2O$ 0.1 g ZnSo$_4$ × 7 H$_2$O
0.1 g MnSO$_4$ × 4 H$_2$O
dissolved in 1000 ml a.dest.
Thiamine-Solution:
  100 mg thiamine × HCl
  dissolved in 1000 ml a.dest.
Adenine-Solution:
  0.275 g adenine
  dissolved in 1000 ml a.dest.
Phenylalanine-Solution:
  1.5 g D.L-phenylalanine
  dissolved in 1000 ml a.dest.
Inductor-Solution:
  1 g 2-aminobenzaldehyde
  dissolved in 100 ml 50% ethanol.
B. Media:
Pre-culture Medium:
  20 g glucose
  2.5 g L-asparagine
  100 ml solution
  10 ml mineral solution
  100 ml adenine solution
  100 ml phenylalanine solution
  fill up with a.dest. to 1000 ml,
  adjust pH value with 1M HCl to pH 5.0
  0.5 ml thiamine solution
  add in sterilely filtered form after treatment in the autoclave.
Main culture medium:
  corresponds to the pre-culture medium with the following addition to 1000 ml:
  10–20 ml in a 1% solution of e.g.
  2-aminobenzaldehyde in 50% ethanol.

I claim:

1. Process for the production of lignolytic enzymes by means of white rot fungi, wherein a culture composed of the fungi of the subclass of the Aphyllophorales is placed in a closed fermentation vessel filled with a nutrient solution and the suspension is gently moved for the production of pellets of Aphyllophorales, such that there cannot be any shearing forces which would destroy the pellets,
    the process comprising producing the enzymes with the addition of yeasts or benzaldehydes, chlorobenzaldehydes, nitrobenzaldehydes, hydroxybenzaldehydes, aminobenzaldehydes, methylbenzaldehydes, diaryls or triaryls, dialkylalkanes, trialkyl alkanes, open-chained or cyclic imines or derivatives of the aforementioned substances as inductive compounds, wherein the induction may take place one time or several times, and wherein the enzymes are subsequently harvested.

2. Process according to claim 1, wherein after the conclusion of the enzyme production, the pellets are separated from the liquid nutrient medium and are returned again into the fementer for the enzyme production.

3. Process according to claim 1, wherein the culture is placed into a fermenter equipped with a stirrer whose paddles can be adjusted, such that no shearing forces occur which destroy the pellets.

4. Process according to claim 1, wherein Phanerochaete chrysosporium with the addition of yeasts is placed into the fermentation vessel.

5. Process according to claim 1, wherein Coriolus versicolor produces the enzymes with the addition of benzaldehydes, chlorobenzaldehydes, nitrobenzaldehydes, hydroxybenzaldehydes, aminobenzaldehydes, methylbenzaldehydes, diaryls or triaryls, dialkylalkanes, trialkyl alkanes, open-chained or cyclic imines or derivatives of the aforementioned substances as inductive compounds, wherein the induction may take place one time or several times.

* * * * *